(12) United States Patent
Ramaprasad et al.

(10) Patent No.: US 7,771,510 B2
(45) Date of Patent: Aug. 10, 2010

(54) FIXED BED HYPERSORBER AND FRACTIONATION OF FLUIDS USING THE SAME

(75) Inventors: Bojanki Satya Govinda Ramaprasad, New Delhi (IN); Davuluri Prahlada Rao, Uttar Pradesh (IN)

(73) Assignees: Gail (India) Limited, New Delhi (IN); India Institute of Technology, Uttar Pradesh (IN)

( * ) Notice: Subject to any disclaimer, the term of this patent is extended or adjusted under 35 U.S.C. 154(b) by 1050 days.

(21) Appl. No.: 10/557,489

(22) PCT Filed: May 19, 2004

(86) PCT No.: PCT/IB2004/001628

§ 371 (c)(1),
(2), (4) Date: Apr. 20, 2006

(87) PCT Pub. No.: WO2004/101114

PCT Pub. Date: Nov. 25, 2004

(65) Prior Publication Data

US 2007/0056910 A1      Mar. 15, 2007

(30) Foreign Application Priority Data

May 19, 2003    (IN) .......................... 705/DEL/2003

(51) Int. Cl.
*B01D 53/02* (2006.01)
(52) U.S. Cl. ................................ 95/96; 95/148; 96/130
(58) Field of Classification Search .................... 95/96, 95/148; 55/418; 96/130
See application file for complete search history.

(56) References Cited

U.S. PATENT DOCUMENTS

| | | | |
|---|---|---|---|
| 1,422,007 A | 7/1922 | Soddy |
| 1,422,008 A | 7/1922 | Soddy |
| 3,192,954 A | 7/1965 | Gerhold et al. |
| 3,732,984 A | 5/1973 | Phillippi |
| 4,013,429 A | 3/1977 | Sircar et al. |
| 4,434,051 A | 2/1984 | Golem et al. |
| 5,026,528 A | 6/1991 | Gal |
| 5,032,150 A | 7/1991 | Knaebel |

(Continued)

FOREIGN PATENT DOCUMENTS

GB        1172724 A        12/1969

OTHER PUBLICATIONS

Da Silva, F.A., et al.; Feb. 2001; "Propylene/Propane Separation by Vacuum Swing Adsorption using 13x Zeolite"; AIChE Journal; vol. 42, No. 2; pp. 341-357.

(Continued)

*Primary Examiner*—Robert A Hopkins
(74) *Attorney, Agent, or Firm*—Oliff & Berridge, PLC

(57) ABSTRACT

The present invention relates to a fixed bed hypersorber having moving ports for injecting and withdrawing fluids which can be used for fractionation of gaseous mixtures in a fixed bed filled with absorbents/adsorbents, where separation is brought about by contacting gaseous mixture in a countercurrent fashion. The moving ports may take the form of pistons or pairs of tubes arranged concentrically, where one of the tubes has a straight slot and the other tube has a helical slot. Rotation of the tubes with respect to each other produces the moving port.

23 Claims, 9 Drawing Sheets

Countercurrent process – Adsorption vs. Absorption

U.S. PATENT DOCUMENTS 6,387,337 B1    5/2002    Pennline et al.

OTHER PUBLICATIONS

Xiu, G., et al; Dec. 2002; "Simulation of Five-Step One-Bed Sorption-Enhanced Reaction Process"; AIChE Journal; vol. 48, No. 12; pp. 2817-2832.

Rao, D.P.; Feb. 1999; "The Futility of Raffinate Reflux Revisited"; Canadian Journal of Chemical Engineering, vol. 77; pp. 74-77.

Clyde Berg; Aug. 25, 1946; "Hypersorption Process for Separation of Light Gases"; AIChE Journal, 42, pp. 665-680.

R. Bacocchi, et al; 1996; "$C_5$ Separation in a Vapor Phase Simulated Moving Bed Unit"; Fundamentals of Adsorption; pp. 76-82.

D. M. Ruthven, et al; 1989; "Counter-Current and Simulated Counter-Current Adsorption Separation Processes"; Chemical Engineering Science, 44, No. 5, pp. 1011-1038.

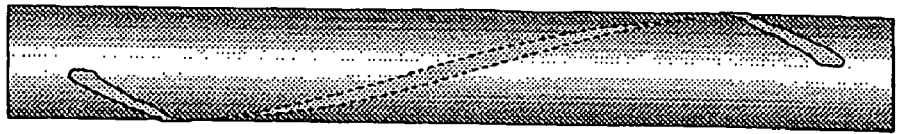
THE OUTER TUBE WITH HELICAL SLOT
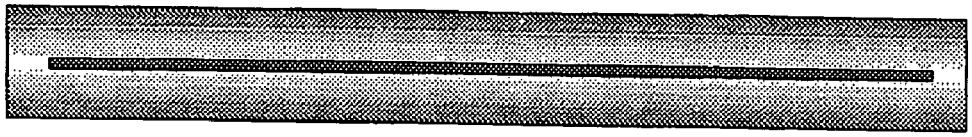
THE INNER TUBE WITH STRAIGHT SLOT
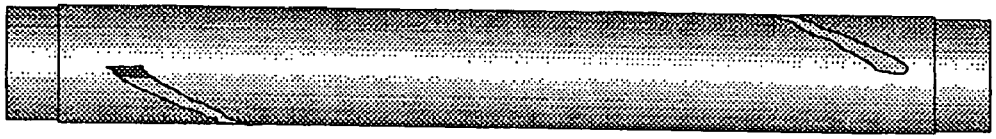
STRAIGHT SLOT TUBE WITHIN HELICAL TUBE
Figure 1a: Moving-port system with straight and helical slots
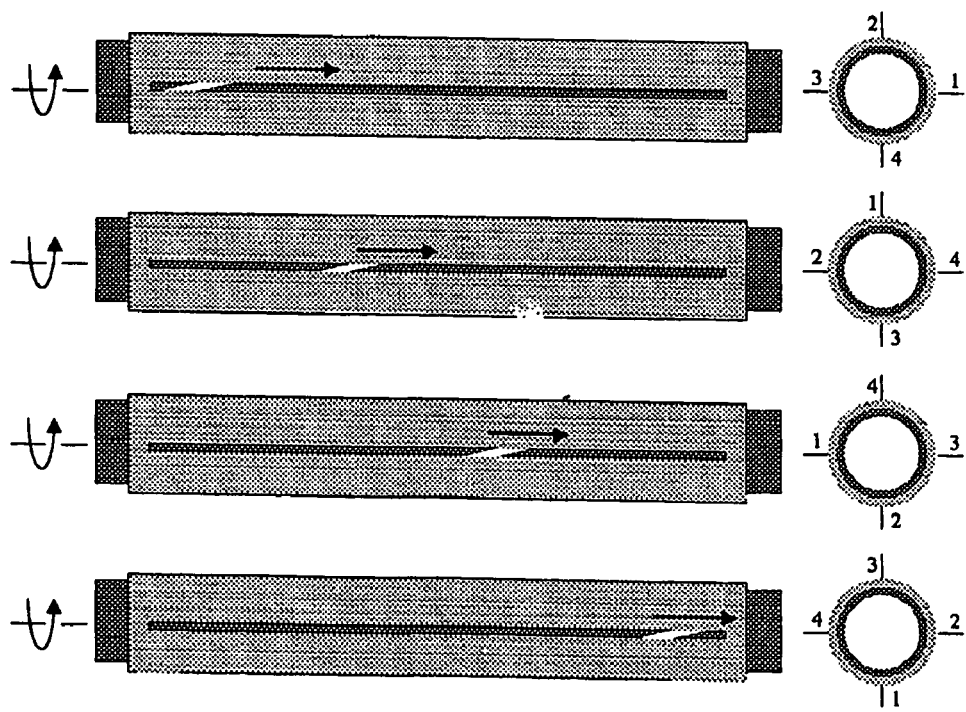
Figure 1b: Sequential Movement of the Port

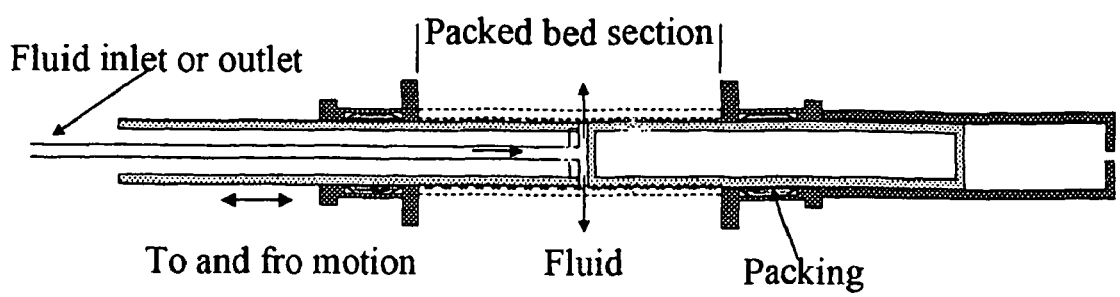
Figure 2: Piston type of moving-port system
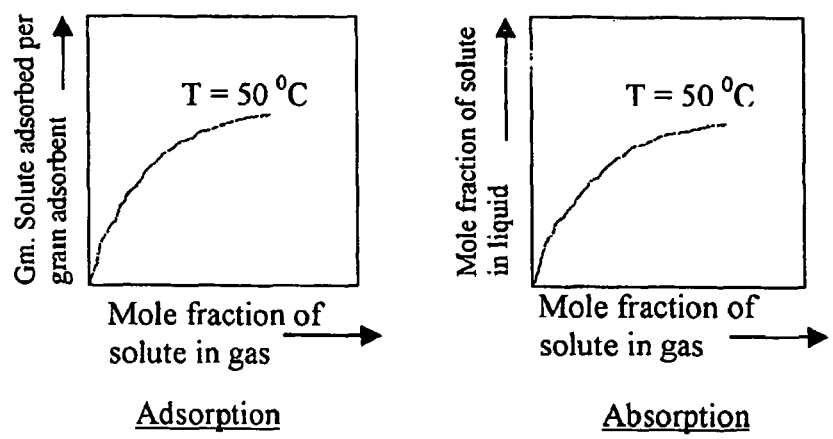
Figure 3: Phase Diagrams – Adsorption vs. Absorption

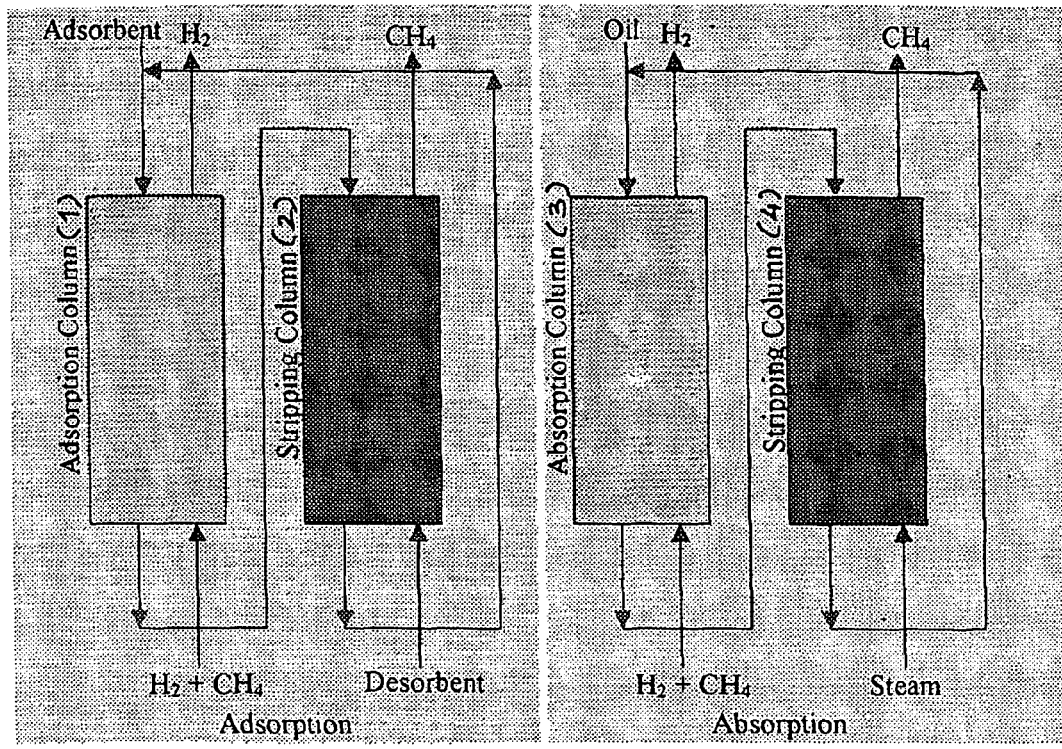
Figure 4: Countercurrent process – Adsorption vs. Absorption
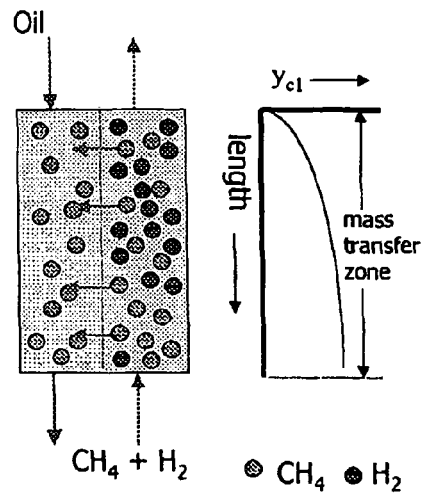
Figure 5: Mechanistic view of Absorption
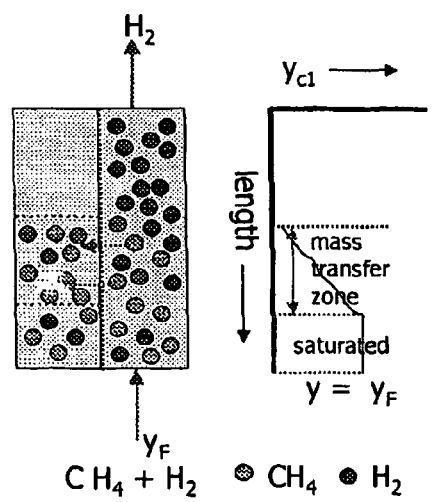
Figure 6: Mechanistic view of fixed bed Adsorption

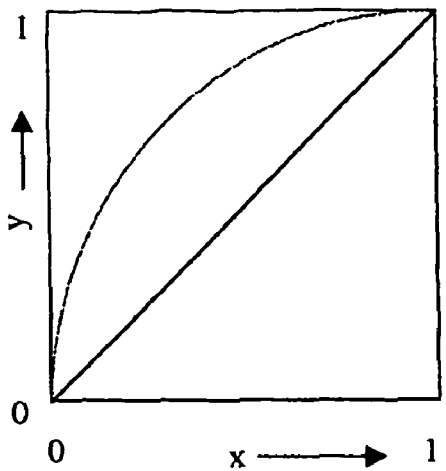
Figure 7: Adsorption Equilibrium for Binary System
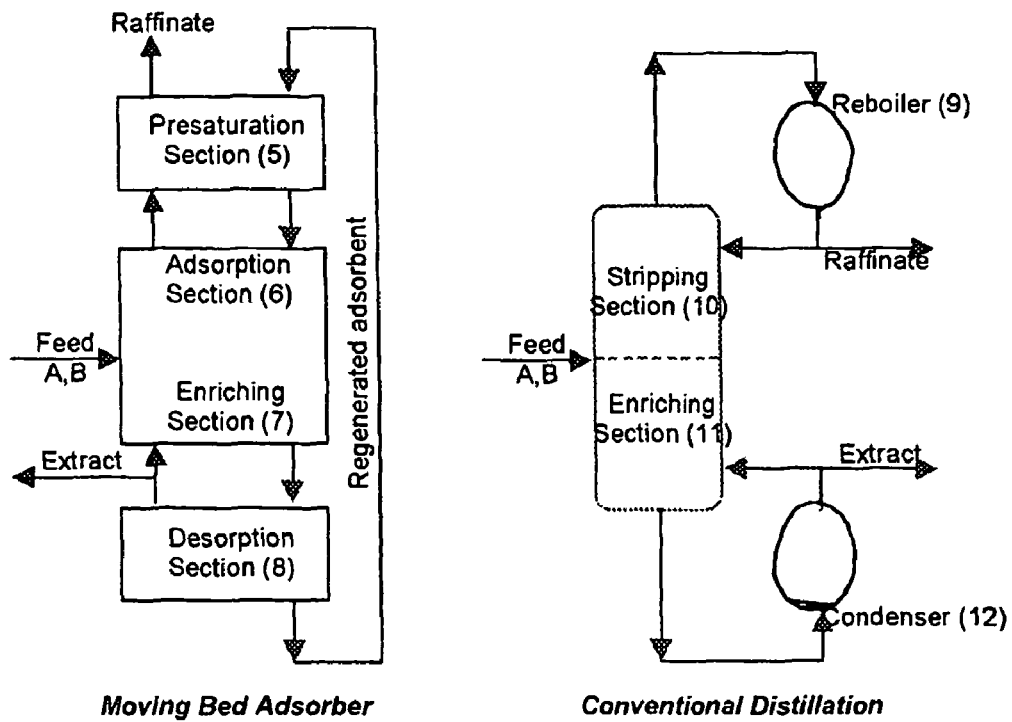
Figure 8: Conceptual Similarity between Adsorption and Distillation

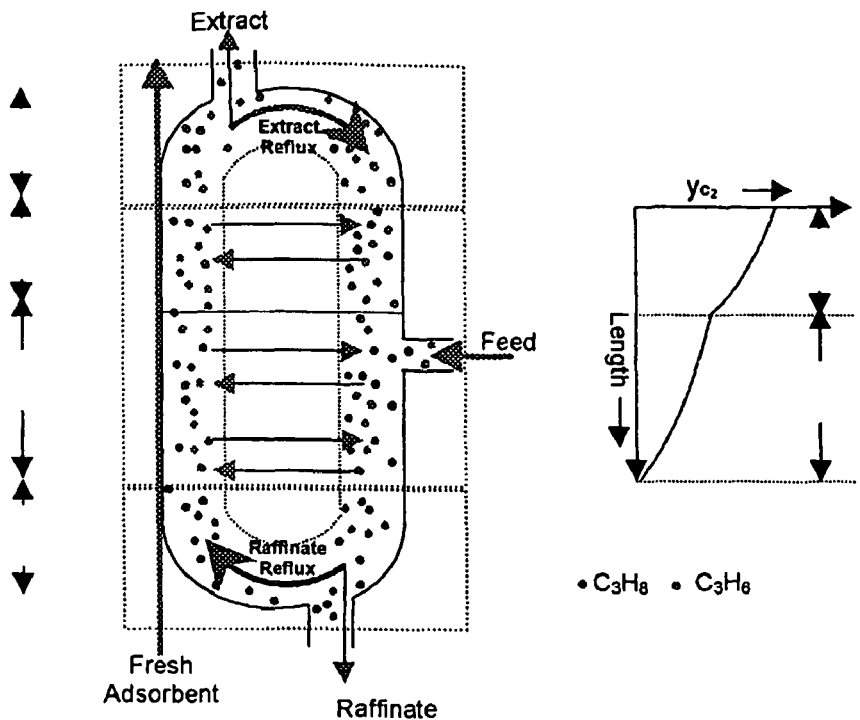
Figure 9: Mechanistic view of Distillation Process
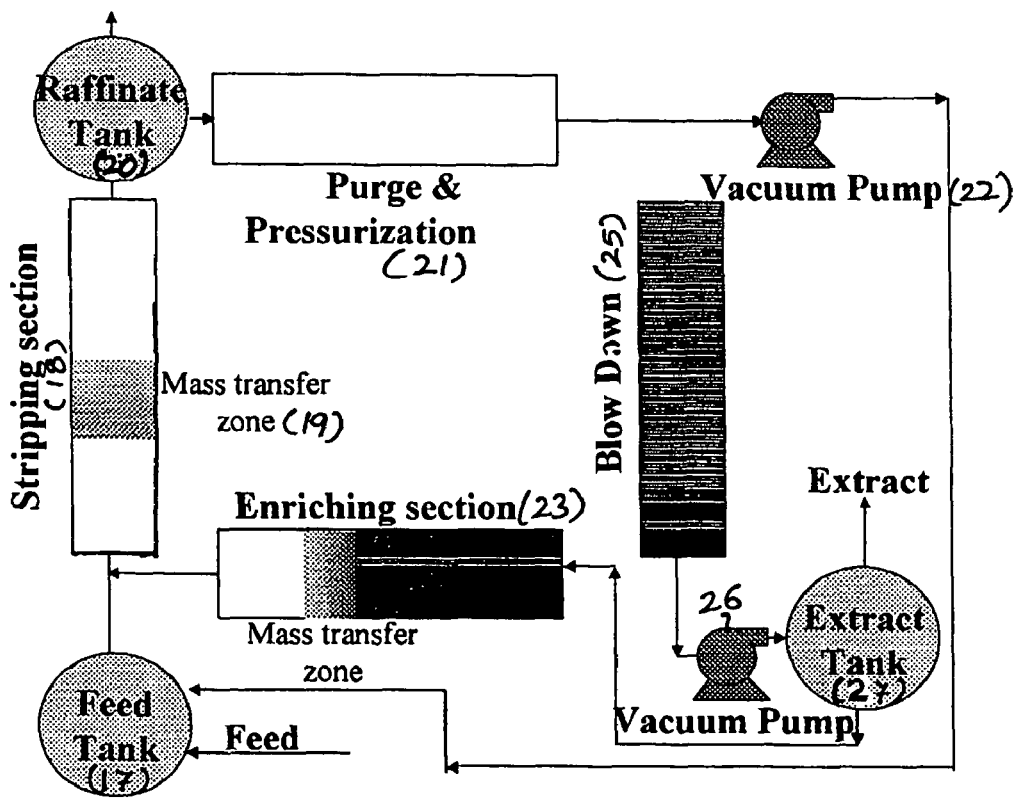
Figure 10: Conditions of Fixed bed Hypersorption process during a Cycle

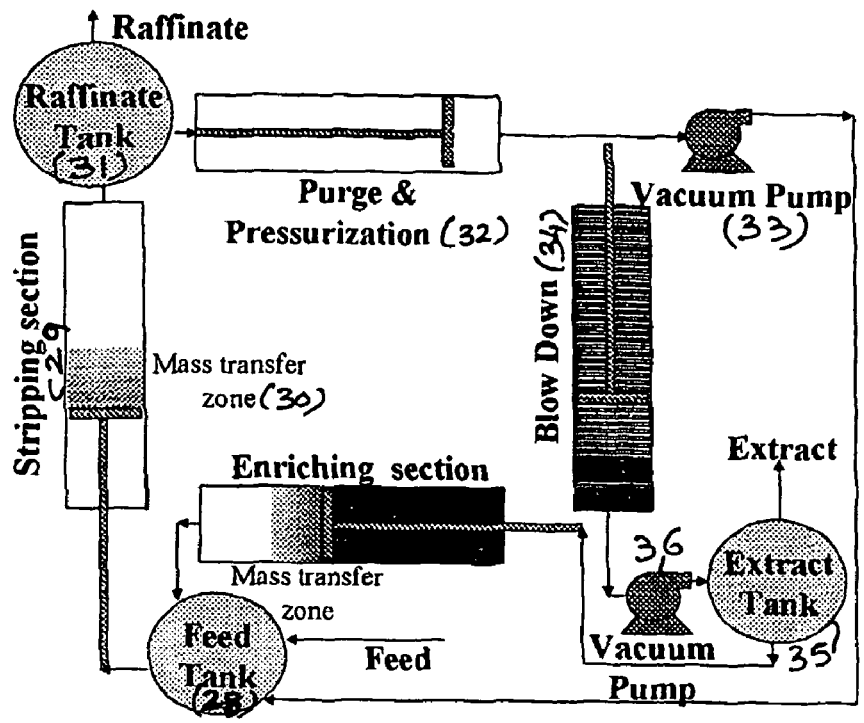
Figure 11: Hypersorber with single moving port in each bed.
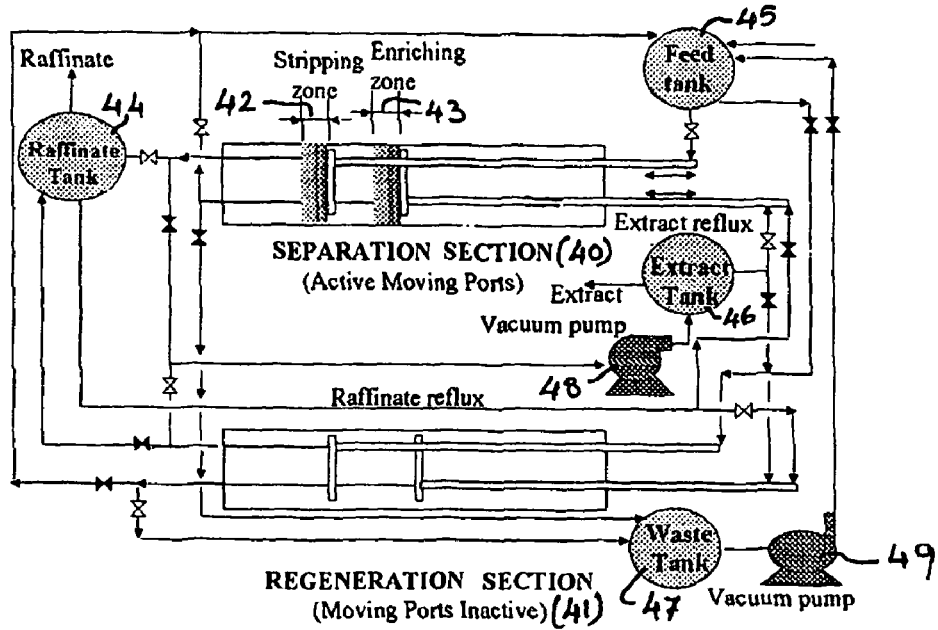
Figure 12: Two Bed Hypersorber with two moving ports in each bed.

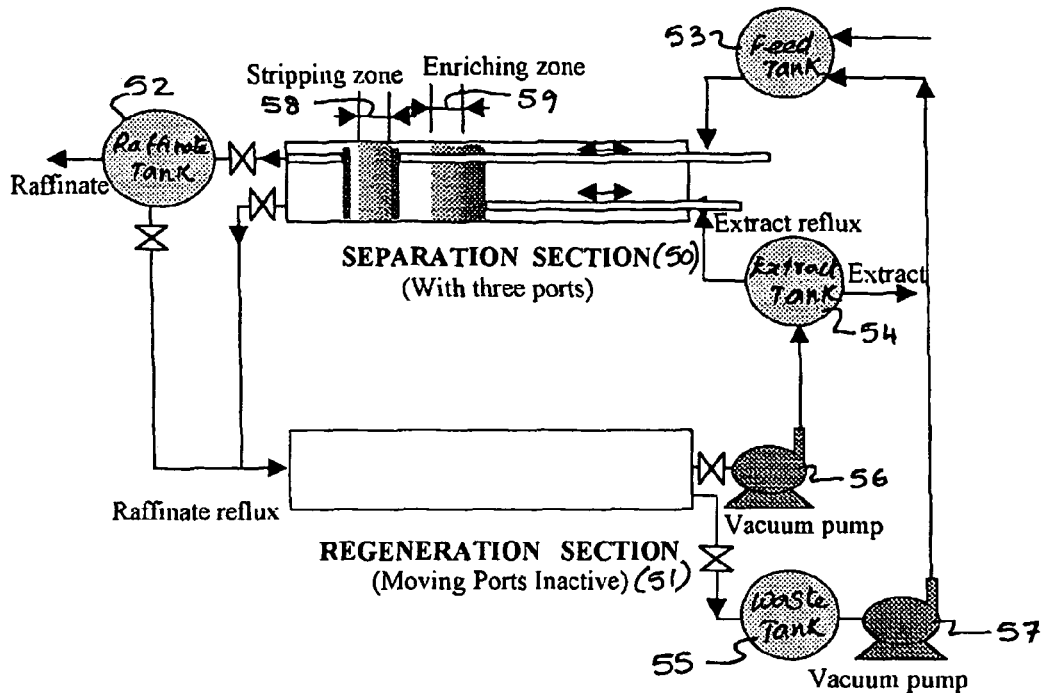
Figure 13: Two Bed Hypersorber with three moving ports in each bed.
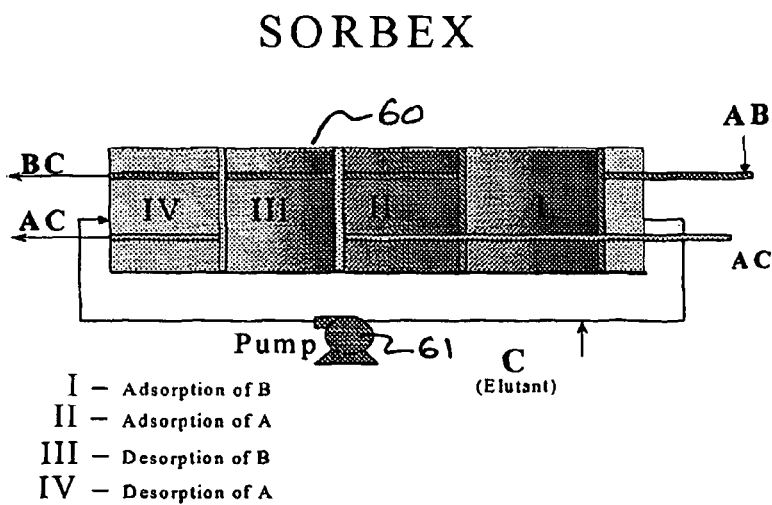
Figure 14: Chromatographic Separation of Liquid Mixtures using Moving Ports.

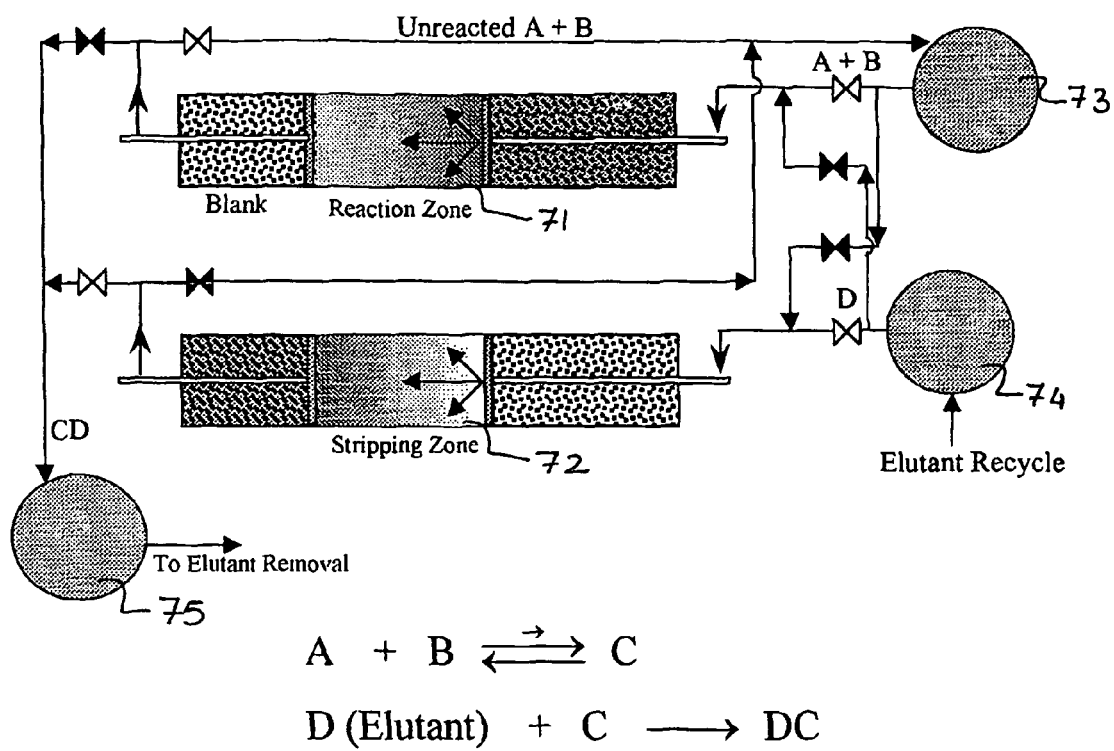
Figure 15: Chromatographic Reactor cum Separator.

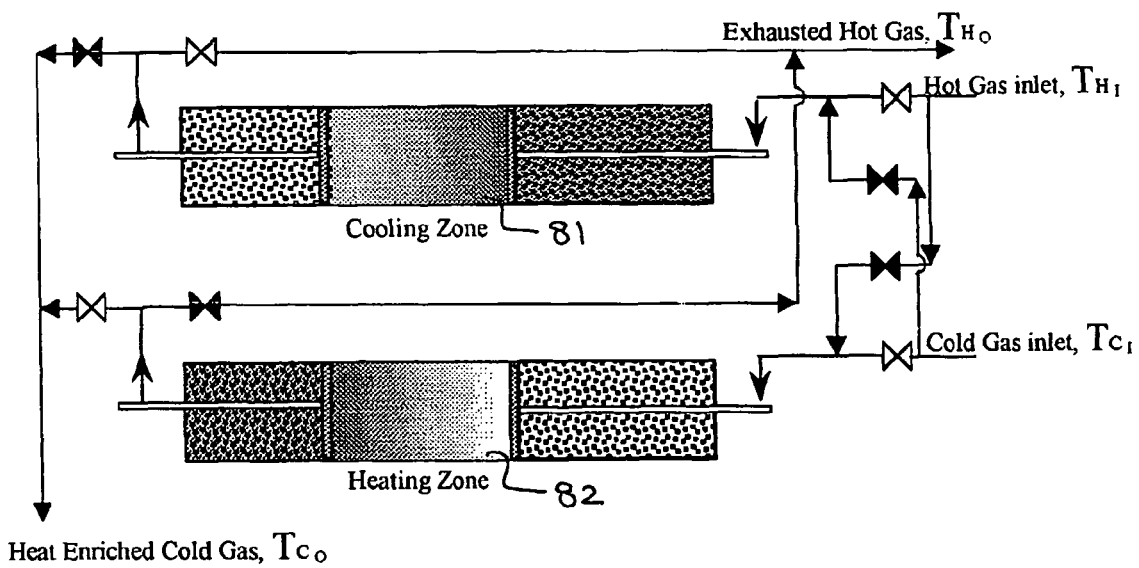
Figure 16: Schematic of single bed heat regeneration with four moving ports.

FIXED BED HYPERSORBER AND FRACTIONATION OF FLUIDS USING THE SAME

TECHNICAL FIELD

The present invention relates to a fixed bed hypersorber having moving ports for injecting and withdrawing fluids. The improved fixed bed hypersorber of the present invention can be used for fractionation of gaseous mixtures in fixed beds filled with adsorbent unlike that in a conventional Hypersorber, where separation is brought about by contacting the gas mixtures in a countercurrent manner with moving adsorbent. The said moving port system effectuates countercurrent solid-gas/solid-liquid contact in a fixed bed. More particularly, the present invention is directed towards two alternate methods of injection and withdrawal of fluids through moving ports—one with the concept of a moving port with helical slots, and the other being a piston type moving port system. The process of contacting the solid-gas/solid-liquid in a countercurrent fashion to emulate a hypersorber in fixed beds is effectuated in the present application either by the moving ports, or by a sequential switching of the fixed beds realized by altering the streams that enter and leave each bed using solenoid valves that could be activated either electrically or pneumatically. The Fixed Bed Hypersorber of the present invention with moving ports can fractionate the gas mixtures into the raffinate and extract products, both with high purity as well as recovery. Series of fixed beds with moving ports can effectuate chromatographic type separation of liquid mixtures with elutant, reaction and separation in tandem and regenerative type heat exchange.

BACKGROUND OF THE INVENTION

Gas separation by moving solids came into existence with the invention of the first continuous adsorption unit invented by F. D. Soddy in 1922 (U.S. Pat. Nos. 1,422,007 and 1,422,008). The renaissance of Soddy's process for the separation of gas mixtures came around 1946, when C. Berg published results on a moving charcoal bed for fractionation of refinery off gases (Berg. C., AIChE Journal, 42, 665 Aug. 25, 1946). The process was named Hypersorption. Hypersorption as a separation process never gained popularity as a sound unit operation to replace conventional operations due to the mechanical problems that persisted in solid handling, mainly the attrition and consequent loss of the by the adsorbents. The hypersorber had distinct zones as in distillation. It had a stripping section and an enriching section above and below the feed point location. It had a two shell and tube heat exchangers; one at the bottom for regenerating the bed by steam heating and another at the top for cooling the hot regenerated adsorbent before the adsorbent is recycled back to the stripping section. Regeneration by heating is known as thermal swing and was employed in the conventional Hypersorber. However in the proposed process the regeneration is done by depressurization\pressure swing.

Separation brought out in manner similar to that of a Hypersorber was not observed and reported in prior works in fixed beds. The separation mechanism and power of Hypersorption has always remained in relative obscurity, and that is why the concept of a Hypersorber was not emulated for gas separation in fixed beds in earlier works. This is possibly because the idea of a unified approach to separation processes has not been conceived, and hence the real concept of Reflux common to all separation processes was not palpable. The concept of reflux on which the proposed process underlies has been discussed extensively in the paper by D. P. Rao—"The Futility of Raffinate Reflux Revisited" (The Canadian Journal of Chemical Engineering, Volume 77, February, 1999). The proposed process can bring about effective fractionation of any gas mixtures (with separation factor even lower than 2) unlike that in the previous works, wherein the fractionation of air alone was claimed and that too with high selectivity adsorbents. In literature for equilibration separation processes the inherent separation factor corresponds to those product compositions which will be obtained when simple equilibrium is attained between the product phases.

A conventional Pressure swing adsorption (CPSA) unit is employed for separation of binary and multicomponent gas mixtures. A CPSA unit basically involves cycles during which few beds are getting loaded with some component of the gas mixture and few beds that are getting regenerated. The cycle is complete when the said activities in the corresponding bed are complete, and the activities that are opposite to that which took place in the earlier cycle are initiated. This repeated loading and regeneration in each bed will end up in a cyclic steady state over a period of cycles and a separation is achieved. When the separation factor is very large (about 10) sharp separation is possible. However, if the separation factor is between 1.5 and 10, sharp separation cannot be achieved. We get one component to be nearly pure but the recovery is poor. For example, separation of propylene (50 mol %) and propane (50 mol %) by PSA yields about 95% propylene, but the yield is low as low as 50%, which means the rest of propylene is lost with propane. Da Silva and Rodrigues carried out a VSA process with 13×Zeolite that could generate a propylene enriched stream of 98% mol relative to propylene/propane mixture, with 3.2% of nitrogen, a recovery of 19%, and productivity of 0.785 mol/kg/h (*Propylene/Propane Separation by Vacuum Swing Adsorption using 13×Zeolite, AIChE Journal*, February 2001 Vo. 47, No. 2). However, the said scheme of fractionation with fixed bed hypersorber like process yields sharp separation; i.e. we get nearly pure propylene and propane. The yield is better than 98%.

Air fractionation in fixed beds has been reported in the patent by Sircar et al. (U.S. Pat. No. 4,013,429) with four steps carried out in two trains (2 beds per train). The four steps that have been reported are—Adsorption, Nitrogen Rinse, Desorption and Presaturation. A patent by Knaebel. K. S (U.S. Pat. No. 5,032,150) claims a six step PSA process for the production of high purity nitrogen, and a product oxygen rich gas from air using a fixed bed. The steps are—Blowdown, Purge, Pressurization, Feed, Pressure Equalization and Rinse.

Fractionation of liquid mixtures is achieved using an elutant (desorbent). These processes are well known as Sorbex processes. The Sorbex process is the generic name for similar processes that carry the UOP's (Des Plaines, Ill., USA) trade names like Parex, Ebex, Molex and Sarex. Morbidelli and his coworkers (see Baciocchi et al. (1996) have demonstrated the fractionation gas mixture using Sorbex process. Ruthven and Ching (1989) presented a state-of-the-art review of the countercurrent and simulated countercurrent adsorbers. In the UOP Sorbex process, a single rotary valve having several ports is used to realize the switching of the ports for the injection or withdrawal of liquid. Several pipes have to be connected to the valve and the bed. The bed needs to be sectionalized. The movement of port is discrete.

Ideally, a continuous countercurrent system should involve a bed of adsorbent moving downward in plug flow and a gas/liquid mixture flowing upward in plug flow through the void space. Unfortunately, due to problems of adsorbent attrition, liquid channeling and non-uniform flow of adsorbent particles; such a system has not been successfully developed. The Inventors have noticed that it is possible to use fluidized beds or moving beds to achieve countercurrency. However, the attendant mechanical complexity involved in handling of solids and the loss of adsorbent due to attrition have inhibited the use of the continuous countercurrent processes. These problems are responsible for the demise of the hypersorption process. As an alternative to the moving bed, UOP developed a simulated periodic moving-bed adsorber with a fixed bed. The input and output ports of the adsorber are periodically switched among sections of the bed to achieve countercurrent contact of solid and liquid phases using a rotary valve (U.S. Pat. No. 3,192,954).

Of late sorption enhanced adsorptive reactors have come to limelight as a good prospect for many industrially important reactions that are limited by equilibrium. Hydrogen synthesis reaction by steam reforming of natural gas and ammonia synthesis reaction from synthesis gas (effluent gas obtained by cracking naphtha or natural gas) are two such reactions whose industrial importance has been widely accepted. Rodrigues et al. (*Simulation of Five-Step One-Bed Sorption Enhanced Reaction Process, AIChE Journal*, December 2002, Vol. 48, No. 12) discusses in detail the modeling and simulation of the steam reforming of natural gas to synthesize hydrogen based on sorption enhanced reaction process. However industrial reactors are normally followed by a huge separation train of varying configurations.

It is felt that fixed bed hypersorber can be suitable for such processes once a proper countercurrent solid-gas/solid-liquid contacting method is devised. Also, such fixed bed hypersorbers can stage process intensification of housing both the reaction as well as separation within a single bed. Thus there is a grave need to develop novel systems for injecting and withdrawing fluids in fixed bed hypersorbers which can effectuate countercurrent solid-gas/solid-liquid contacting.

OBJECTS OF THE PRESENT INVENTION

The main object of the present invention is to emulate the moving bed hypersorber in a fixed bed hypersorber.

Another object of the present invention is to provide a fixed bed hypersorber having moving ports for injecting and withdrawing fluids which effectuates countercurrent solid-gas/solid-liquid contacting.

Yet another object of the present invention is to realize moving bed hypersorber in a fixed bed hypersorber by moving the inlet ports or by sequential switching the streams that enter and leave each bed.

Still another object of the present invention is to effectively fractionate any gas mixture into two product streams—the Raffinate product stream and the Extract product stream. One more object of the present invention is to effectively fractionate any gas mixture into two streams—the Raffinate stream and the Extract stream in four fixed beds using five steps that are staggered in between the beds in such a way the process is continuous.

One another object of the present application is to effectuate process intensification with only two fixed beds in the claimed method for gas mixture fractionation, rather than with four fixed beds.

It effectuates chromatographic separation of liquid mixtures in a fixed bed using an elutant. Sorbex like process performed with moving ports rather with rotary valves.

It effectuates single\multiple bed reactor cum separator, using the concept of moving ports.

It effectuates effective heat exchange between a hot gas stream and a cold gas stream across the bed of solids using the concept of heat regeneration, i.e. it accomplishes a twin bed regenerative heat exchanger using the concept of moving ports.

SUMMARY

A method to emulate the moving fluidized bed hypersorption process in fixed beds has been conceived by incorporating moving port system in the presently available fixed bed system. The hypersorber had a bed of adsorbent moving downward in plug flow and a gas/liquid mixture flowing upward in plug flow through the void space. The moving ports bring about countercurrent solid-gas/solid-liquid contact in the fixed bed. Two methods of injection and withdrawal of fluid from the moving ports have been conceived. The first method is with helical slots, and the other being a piston type moving port system. The said moving-ports enable to move continuously the ports of injection or withdrawal of liquid or gas across the entire bed. The said moving-ports can be used to design simulated moving beds for separation of gas and liquid mixtures and also to effectively exchange heat between gases. The motive behind the moving port concept is to bring about process intensification in the process that is being claimed for gas mixture fractionation, and also in the development of regenerative heat exchangers using moving ports. The streams that enter and leave each fixed bed can also be switched sequentially using solenoid valves that could be activated either electrically or pneumatically to realize the process of contacting the solid-gas/solid-liquid in a countercurrent fashion.

BRIEF DESCRIPTION OF THE ACCOMPANYING DRAWINGS

In the drawings accompanying the specification,

FIG. 1(*a*) represents the moving-port system with straight and helical slots.

FIG. 1(*b*) represents sequential movement of the port.

FIG. 2 represents the piston type of moving-port system

FIG. 3 represents the phase diagrams—adsorption vs. absorption

FIG. 4 represents the countercurrent process—adsorption vs. absorption

FIG. 5 represents the mechanistic view of absorption

FIG. 6 represents the mechanistic view of fixed bed adsorption

FIG. 7 represents the adsorption equilibrium for binary system

FIG. 8 represents the Conceptual similarity between adsorption and distillation.

FIG. 9 represents the mechanistic view of distillation process.

FIG. 10 represents the conditions of fixed bed hypersorption process during a cycle.

FIG. 11 represents the hypersorber with single moving port in each bed.

FIG. 12 represents the two bed hypersorber with two moving ports in each bed.

FIG. 13 represents the two bed hypersorber with three moving ports in each bed.

FIG. 14 represents the chromatographic separation of liquid mixtures using moving ports FIG. 15 represents the chromatographic reactor cum separator FIG. 16 represents the schematic of single bed heat regeneration with four moving ports.

DETAILED DESCRIPTION OF THE INVENTION

Accordingly, the present application provides a fixed bed hypersorber effectuating countercurrent solid-gas/solid-liquid contacting, said hypersorber comprising:
- a column comprising solid absorbent/adsorbent material in the form of packed bed section, and one or more moving port fluid injection and withdrawal systems incorporated inside the column for injecting and withdrawing the gas/liquid to be purified.

In an embodiment of the present application, the moving port fluid injection and withdrawal system comprises of conduit or piston moving in to and fro direction through the column comprising the solid absorbent/adsorbent.

In another embodiment of the invention, the moving port fluid injection and withdrawal system comprises of a pair of tube arranged in a concentric fashion, wherein one of the tubes is provided with a straight slot and the other tube is provided with a helical slot, and both the tubes are rotated with respect to each other by means of a motor.

The present also provides a method for fractionation of a mixture of fluids, said process comprising the steps of:
- (a) passing the mixture of fluids to be fractionated through one or more hypersorbers provided with one or more variable inlet means for influx of the mixture of fluids, one or more fixed beds filled with one or more adsorbers being placed in proximity of the inlet means, and at least two outlets means through which the fractionated fluids can be withdrawn;
- (b) introducing the mixture of fluids to be fractionated into the variable inlet means in order to form an axial and radial flow of the fluids, wherein the axial and radial flow of the mixture of fluids is such that the fluids come out of the inlet means from different controllable locations;
- (c) contacting the mixture of fluids to be fractionated coming out of the variable inlet means with the fixed bed filled with the adsorbers to adsorb a raffinate component from the mixture of the fluids and to provide a substantially pure extract component;
- (d) removing the substantially pure extract component of step (c) from at least one of the said outlet means, and
- (e) removing the fixed adsorbent bed having the raffinate component adsorbed on it and de-adsorbing the raffinate component from the bed to obtain substantially pure raffinate component.

In another embodiment of the present application, the mixture of fluids to be fractionated is selected from the group consisting of a mixture of two or more gases, a mixture of one or more gases and one or more liquids and a mixture of two or more liquids.

In yet another embodiment of the present application, the mixture of fluids to be fractionated is selected from the group consisting of a mixture of two or more gases and a mixture of one or more gases and one or more liquids.

In still another embodiment of the present application, the variable inlet means for influx of the mixture of fluids is a hollow movable piston with a piton head wherein said piston head is provided with plurality of holes.

In one more embodiment of the present application, the holes are provided on a circumferential side of the piston head.

In one another embodiment of the present application, the hollow piston is connected to a supply of the mixture of fluids.

In a further embodiment of the present application, the mixture of fluids are fed to the piston at elevated pressure.

In a further more embodiment of the present application, the piston is attached to a motor through a connecting means for providing back and forth motion to the piston.

In another embodiment of the present application, the piston is attached to a motor through a linear screw for providing back and forth motion to the piston.

In yet another embodiment of the present application, the variable inlet means for influx of the mixture of fluids comprises of a pair of tubes arranged in a concentric fashion and being provided with one or more slots.

In still another embodiment of the present application, the variable inlet means for influx of the mixture of fluids comprises of a pair of concentric tubes wherein an inner tube is provided with a traverse slot running parallel to a vertical axis of the tube and an outer tube provided with a helical slot running parallel to a vertical axis of the tube or vice versa such that a trapezoidal opening is formed where both the slots overlap.

In one more embodiment of the present application, the outer tube is rotated with respect to the inner tube to move the trapezoidal opening from one end of the tube to the other.

In one another embodiment of the present application, the variable inlet means for influx of the mixture of fluids comprises of a pair of tubes arranged in a concentric fashion such that an inner tube is provided with a series of valves on its outer surface and an outer tube is provided with a means for opening the valves in a predetermined fashion on its interior surface.

In a further embodiment of the present application, the variable inlet means for influx of the mixture of fluids comprises of a pair of tubes arranged in a concentric fashion such that an inner tube is provided with a series of push-button valves on its outer surface and an outer tube is provided a helical strip on its interior surface for opening the valves in a sequential fashion.

A fixed bed hypersorber like process has been proposed that can be realized with or without moving ports for the fractionation of gaseous mixtures in fixed beds filled with absorbent.

The regeneration of the fixed beds is done using pressure swing and the process involves concurrent reflux of both products, namely the Extract Reflux and Raffinate Reflux. The extract reflux is a continuous reflux. The Raffinate reflux however is discrete, i.e. the effect of raffinate reflux similar to distillation is realized only after the High Pressure Raffinate Reflux Step in a cycle is over, and when the bed which underwent this step is switched for the High Pressure Adsorption\Stripping Step. The said process can fractionate the gas mixtures into the Raffinate and Extract products, both with high purity as well as recovery. The process accomplished with\without moving ports in fixed beds for gas fractionation has five steps. The steps are—High Pressure Adsorption\Stripping step, High Pressure Extract Reflux/Enriching step, Low Pressure Regeneration Step, Low Pressure Raffinate Recycle step, and High Pressure Raffinate Reflux step. During any moment of the process—adsorption, enriching, and regeneration steps occurs in an individual bed each; and the Raffinate Recycle step at low pressure and Raffinate Reflux step at high pressure occurs in a same bed. The said steps are staggered in between the beds in such a way the process is made continuous. The said staggering is possible by the excitation and non-excitation of normally closed solenoid valves in a sequential and systematic manner.

The Inventors have now invented moving-ports, and two methods by which the port of injection or withdrawal of liquid or gas is continuously moved in a controlled fashion, thereby achieving countercurrent action. The said injection and withdrawal of fluids using moving ports accomplish the realization of countercurrent solid-gas contact in moving beds with fixed beds only. The moving ports can be used to design simulated moving beds for separation of gas and liquid mixtures and also to effectively exchange heat between gases. The two types of moving ports developed in the present application for effecting the countercurrent contacting of solid-gas or solid-liquid are (a) helical slot moving port system, and (b) piston type moving port system. The said moving ports can accomplish a Hypersorber like process in fixed beds. Depending on the type of gas mixtures the said ports can bring out—fractionation of gas mixtures in four beds, and absorption like separation in three beds. The former case can be accomplished with two fixed beds only when used with three moving ports in each bed, and results in process intensification. If the process intensification is compromised the fractionation will occur in fixed beds without moving ports.

The streams flowing in and out of the four beds are sequenced such that exact flow sequence occurring in the moving bed hypersorber is emulated in the fixed-bed hypersorption like PSA. The steps are—High Pressure Adsorption\Stripping step, High Pressure Extract Reflux/Enriching step, Low Pressure Regeneration Step, Low pressure Raffinate Purge with Total Recycle, and High Pressure Raffinate Reflux step. This flow coordination actually stages fractionation of any gas mixture like that in a moving bed hypersorber, and this is unlikely of any existing conventional PSA systems.

For binary gas mixtures the said process can bring about effective fractionation into two highly pure product streams with excellent recoveries. For example—a binary mixture of ethane and ethylene can be effectively fractionated using the said process to yield highly pure ethane as the Raffinate product and highly pure ethylene as the Extract product with excellent recoveries at both ends. For multicomponent gas mixtures the said process can bring about fractionation in such a manner that either the light component is taken as the pure Raffinate Product, or the intermediate components along with the heavy component is drawn as the Extract Product, or the vice-versa. For example—a ternary mixture of methane, ethane and propane can be fractionated using the said process to yield highly pure methane as the Raffinate product, or highly pure propane as the Extract product. Multi-component mixtures can be also be fractionated at desired cuts in the said process.

1. Novel Idea on the Concept of Moving Ports

The Inventors have invented moving-ports, which enable the user to move continuously the ports of injection or withdrawal of liquid or gas. These can be used to design simulated moving beds for separation of gas and liquid mixtures and also to exchange heat between gases. The Inventors have proposed two methods of injection and withdrawal of fluid mixtures using moving ports.

Method-1:

The first type of moving-port system is shown in FIG. 1a. This system has an inner tube with a straight slot and an outer tube with helical slot. The slots can be placed the other way around also. Where these slots intersect a rhombus shaped port or opening is formed. If one of these tubes is rotated, the port moves from one end to the other and returns abruptly. The stepper motor or motor with a gear train or other means can be used to rotate the outer tube. The inner tube can be connected to a fluid line. A fluid can be introduced or withdrawn through the port. The gasket can be fixed around the slots to prevent leakage through slots from the portion other than the opening. Introducing or withdrawing fluid through a port amounts a 'point' feed or withdrawal.

It is also possible to have a line feed or withdrawal, which may be advantageous in some cases. Such moving-port systems can be embedded in packed beds to achieve countercurrent processes. The sequential movement of the port has been shown in FIG. 1b.

Alternately, one of these tubes can be fixed with a number of push-button valves. These valves can be opened using a helical strip fixed on the other tube to realize the moving-port operation. The later version can be used where even a minor leak of liquid or gas from the portion other than port has severe detrimental effect.

Method-2:

The second system is a piston type of moving-port system. Sketch of this version is given in FIG. 2. The piston type moving-port system comprises a outer perforated tube and an inner movable tube. Inner one is a loose fitting tube with one end closed. In between the ends, a smaller tube is fixed to so as to feed liquid or gas as shown in figure. The fluid moved back and forth using a linear screw and motor with suitable arrangement. The movement of the inner tube is such that the port can be smoothly moved from one end to the other. Unlike the system with slots, the port has to be drawn back to restart the operation. It is possible to have a leak-proof system.

A single system can be used to inject or withdraw fluid from more than one point. The moving-port systems can be used to build moving-bed adsorber, combination reactor and separators or heat exchangers.

2. Mechanism of Separation

For the sake of clarity, we consider here separation mechanism of a binary gas mixture. The conventional PSA is a kin to absorption. Only one of the components gets adsorbed as with the $H_2$—$CH_4$ mixture or the separation factor has to be very high for effective separation. On the other hand, the proposed Hypersorber like process accomplished in fixed beds with or without moving ports is a kin to distillation. It is effective for separation of mixtures with separation factor as low as 1.5. There are several systems for which the separation factor is in between 1.5 to 15 (see, Myers). The said process can fractionate binary mixtures into two product streams and can bring about sharp separation as in distillation.

In the following we have the similarities between absorption and conventional PSA on one hand, and distillation and Fixed bed Hypersorber with moving ports on the other. Though, these are well known, they are presented to set Fixed bed Hypersorber with or without moving ports in a proper perspective.

Absorption and Conventional PSA

The phase diagrams for absorption and adsorption where only one component (solute) gets transferred into solvent or adsorbent is given FIG. 3.

The corresponding countercurrent processes are shown in FIG. 4. The binary mixture of the $H_2$ and $CH_4$ is passed through an adsorption column (1) from one end and an adsorbent is passed through the adsorbent column through the other end. $CH_4$ present in the mixture will adsorbed to the adsorbent and $H_2$ is removed from the end through which the adsorbent is fed. The adsorbent having $CH_4$ adsorbed thereto is removed and fed to a stripping column (2) from its top and a desorbent is fed from the bottom of the stripping column. The $CH_4$ is desorbed and removed, while the pure adsorbent thus obtained is recycled to the adsorbent column. Before feeding the adsorbent, the same is regenerated by pressure or thermal swing or elution. The process of absorption is also shown in FIG. 4. In the absorption process, a solvent is passed through the absorption column (3) and the mixture of mixture of the solution thus obtained from the absorption column is fed to a stripping column (4) wherein a solvent is removed and the solvent thus obtained is regenerated by steam stripping, which can be viewed as thermal swing combined with elution or it can be done by pressure swing.

FIGS. 5 and 6, shows the mechanism of separation in absorption and in a bed of conventional PSA. The yellow region represents the solvent or adsorbent phase and the blue region represents the gas phase. The colored spots represent gas molecules and roughly their density in the gas and solid phases.

Distillation and Fixed Bed Hypersorber with or without Moving Ports

The comparison of fractionation achieved by distillation to that achieved by moving-bed adsorption has been discussed first. The phase diagrams of both are similar and the phase diagram of binary system adsorption has been shown in FIG. 7.

The conceptual similarity between Adsorption and distillation has been shown in FIG. 8. Both processes have enriching section (7 and 11) and stripping section (6 and 10) in common. The Presaturation section (5) in adsorption is similar to the reboiler (9) in distillation and desorption section (8) in adsorption is similar to condenser (12) in distillation. The actual fractionation takes place in the enriching and stripping sections. The mechanism of separation is shown in FIG. 9. More details are given elsewhere (Rao, D. P., "The futility of Raffinate Reflux Revisited", Cand. J. Chem. Engg).

The moving-bed operation is emulated in four fixed beds and is analogous to a Hypersorption like process carried out in fixed beds. The 'operation' of the fixed bed Hypersorption like process is similar to conventional PSA and operates in a cyclic manner. The cycle has five steps. During a cycle, each bed goes through High Pressure Adsorption\Stripping step, High Pressure Extract Reflux/Enriching step, Low Pressure Regeneration Step, Low pressure Raffinate Purge with Total Recycle, and High Pressure Raffinate Reflux step. The conditions of the beds in all four steps are shown the FIG. 10. The Feed is stored in feed tank (17) and from there is it fed to a stripping section (18) having a mass transfer zone (19), the raffinate is obtained from the top of the stripping section and is stored in a raffinate tank (20). The thus stored raffinate is fed to a purge and pressurization section (21). A vacuum pump (22) is connected to the output of the purge and pressurization section which draws the contents from this section and feeds it to the feed tank (17). Once the stripping process is complete, the stripping section is taken up for blow down process. In the blow down process, the extract is obtained from the adsorbent/absorbent contained in the blow down section (25), and stored in an extract tank (27) using a vacuum pump (26). Thereafter the section is enriched in an enriching process to obtain an enriched section (23) which is ready for use in stripping process.

The lengths of mass transfer zones of each of the sections are only a few centimeters as is the case with the conventional PSA.

In the ideal case wherein there is complete regeneration of adsorbent. Then the bed that undergoes regeneration by pressure swing is identical to condenser in its function. Then, the Low pressure Raffinate Purge with Total Recycle is not required. The mixture can be separated into pure components. However in practice, complete regeneration is not possible. Therefore, the Low pressure Raffinate Purge with Total Recycle is required to get nearly pure products. Our simulation studies show that, the Low pressure Raffinate Purge with Total Recycle can be adjusted such that the composition of the stream at the end of this step is same as the feed and it can be recycled after being compressed along with feed. Thus, we ensure that there is no waste stream. The recycle is valuable if the components are of high economic value.

As with distillation, we have concurrent reflux at both ends—extract reflux and raffinate reflux. They are not independent. They are linked in a manner as the boil-up ratio and reflux ratio in distillation. For specified separation, there is a minimum reflux ratio. This can be accurately found on the diagram similar to the Ponchon-Savarit diagram or approximately on the McCabe-Thiele diagram. We can find the optimum reflux ratio based on the economic analysis. We can use the Underwood equation to determine the reflux ratio for multicomponent mixtures.

In distillation, the separation factor is usually referred as the relative volatility. As the relative volatility tends infinity the minimum reflux ratio tends to zero and the distillation tends to stripping process. The same is the case in adsorption. The fractionation tends to the simple stripping as is the case with the $H_2$—$CH_4$ mixture. We can separate this mixture into pure $H_2$ and pure $CH_4$, in principle, with three columns employing the total recycle of Low pressure Raffinate Purge stream.

3. A Fixed Bed Hypersorber Like Process with Moving Ports 3.1 Four-Bed Hypersorber with Single Moving-Port in Each Bed.

Hypersorber with one moving-port in each bed has been shown in FIG. 11. The moving-ports are depicted as a piston pushing the mass transfer zone. However the process can be carried out in more than four beds or less than four beds depending on the nature of the gas mixture that is to be fractionated and the degree of process intensification that one looks for. The feed containing a binary mixture is stored in feed tank (28) and from there is it fed to a stripping section (29) having a mass transfer zone (30), the raffinate is obtained from the top of the stripping section and is stored in a raffinate tank (31). A part of the raffinate thus obtained is fed to a purge and pressurization section (32). A vacuum pump (33) is connected to the output of the purge and pressurization section which draws the contents from this section and feeds it to the feed tank (28). Once the stripping process is complete, the stripping section is taken up for blow down process. In the blow down process, the extract is obtained from the adsorbent/absorbent contained in the blow down section (34), and stored in an extract tank (35) using a vacuum pump (36). Thereafter the section is enriched in an enriching process to obtain an enriched section (37) which is ready for use in stripping process.

3.2 Two-Bed Hypersorber with Two Moving-Port Systems in Each Bed

The schematic of the arrangement is shown in FIG. 12. In this scheme two mass transfer zones are accommodated in a single bed. Such a system comprises only two section working together. One of the section is called a separation section (40), while the other section is called a regeneration section (41). The separation section is divided into a stripping zone (42) and an enriching zone (43), whereas the regeneration section is divided into blow down zone and a purge and pressurization zone (not shown in FIG. 12). Both these sections are connected to a raffinate tank (44), a feed tank (45), an extract tank (46), and a waste tank (47) using pumps (48 and 49). While the fractionation is taking place in one bed (with active moving ports), the other bed (with inactive moving ports) is undergoing the pre-saturation steps with the Raffinate product.

3.3 Two-Bed Hypersorber with Three Moving-Port Systems in Each Bed

The beds with three moving ports are similar to previous case except that there are three moving-ports in each bed. This scheme typically emulates the SMB unit. In this scheme the ports movement is visualized as the movement of the bed. A typical configuration has been shown in FIG. 13. Here the separation section (50) as well as the regeneration section (51) are connected to the raffinate tank (52), the feed tank (53), the extract tank (54) and the waste tank (55) through 2 vacuum pumps (56 and 57). The separation section is divided into stripping zone (58) and enriching zone (59) whereas the regeneration section is divided into blow down zone and a purge and pressurization zone (not shown in FIG. 13). The stripping and enriching mass transfer zones along with the Regeneration step of the above scheme has been simulated and the results given below.

In FIG. 11, the bed prior to undergoing High Pressure Adsorption\Stripping step is pre-saturated with the light component, i.e. the Raffinate Product, by the Low Pressure and High Pressure Raffinate Reflux step. The gas mixture to be fractionated is fed to the bed undergoing High Pressure Adsorption\Stripping step from a feed tank through the moving port. During this step the Light component pre-saturated in the solid phase is stripped out of it by the adsorption of the heavy component in the feed into it. Light component Stripping takes place along the bed across a mass transfer zone that is developed during this step. A stream highly rich in the light component can be drawn as the Raffinate Product if the said mass transfer zone does not break through across the bed. The said Raffinate product is collected in Raffinate tank. The High Pressure Adsorption\Stripping step is stopped before the breakthrough of the said mass transfer zone occurs. After the High Pressure Adsorption\Stripping step the bed is saturated with feed composition.

In the bed undergoing the High Pressure Extract Reflux/Enriching step, a predetermined portion of the Extract product stream highly rich in the heavy component is refluxed into the bed from the Extract tank using a moving port. The reflux is made in a direction co-current to the direction of feed in the High Pressure Adsorption\Stripping step. Initially this bed is saturated with feed composition by the High Pressure Adsorption\Stripping due to the adsorption of the heavy component and displacement of the light component out of it. Heavy component enriching takes place along the bed across a mass transfer zone that is developed during this step. This step is stopped when the said mass transfer zone break through across the bed. After the High Pressure Extract Reflux/Enriching step the bed is saturated with the Heavy Component both in the solid and gas phase. The stream coming out of this bed is recycled back to the feed tank.

In bed undergoing Low Pressure Regeneration Step, the regeneration of the bed saturated with the Heavy Component is accomplished by using a vacuum pump to perform the pressure swing. The regeneration is performed in a direction co-current to the direction of feed in the High Pressure Adsorption\Stripping step. The heavy-component discharged during the regeneration is drawn as the Extract product into the Extract tank. A portion of the extract product is compressed and used for reflux in the High Pressure Extract Reflux/Enriching step.

Both the Low pressure Raffinate Purge with Total Recycle step and High Pressure Raffinate Reflux step are performed in a single bed. Initially the bed regenerated by pressure swing in the previous cycle is refluxed with a predetermined quantity of the Raffinate Product. The exit stream during this step can be recycled to the feed tank, or could be vented out. The Low pressure Raffinate Purge with Total Recycle step is performed at the regeneration pressure. The Low pressure Raffinate Purge with Total Recycle step is stopped by stopping the withdrawal of the said stream to the feed tank. During the High Pressure Raffinate Reflux step the reflux of the Raffinate product to the bed is continued. Both the Low pressure Raffinate Purge with Total Recycle step and High Pressure Raffinate Reflux step are performed in a direction co-current to the direction of feed in the High Pressure Adsorption\Stripping step. The Low Pressure and High Pressure Raffinate Reflux step pre-saturates the bed with the light component.

The beds undergoing the High Pressure Adsorption\Stripping step and Pressure Extract Reflux/Enriching step are similar to the adsorption and the enriching sections of a conventional Hypersorber. The bed undergoing Low Pressure Regeneration Step is similar to the steam heater in the conventional Hypersorber, the difference only being in the mode of regeneration. While thermal swing has been employed in the conventional Hypersorber for regeneration, pressure swing has been employed for regeneration in our process. The bed undergoing the Low pressure Raffinate Purge with Total Recycle step and High Pressure Raffinate Reflux step is similar to the cooler in a conventional Hypersorber. Thus the process being claimed accomplishes a true Hypersorption like process in four fixed beds using one moving port in each bed.

What is shown in figure is one step of the four steps in a cyclic operation. There are four steps. In a cycle, each bed undergoes all the five steps in that sequence (in sequence as listed above). A cycle is said to have been completed when each bed completes the entire five steps. The time to perform a cycle is defined as the cycle time. By sequential excitation and non-excitation of normally closed solenoid valves, we will be able to realize the cyclic operation. The proper choice of flow rates of the streams is essential to realize the sharp separation. Such a choice is not obvious. We have obtained the possible separations using computer simulations for three systems for cases wherein the moving ports are held stationary at a position in each bed and the results have been tabulated in Tables 1-3.

TABLE 1

Propane-propylene system, Isothermal, D = 50% F, $P_H$ = 1 atm, $P_L$ = 0.01 atm

| Run | F*$10^4$ (mol/s) | D*$10^4$ (mol/s) | $R_E$ | $XC_3H_6$ (%) | $1-XC_3H_8$ (%) | $C_3H_6$ Recovery % | Productivity (mol/kg-h) |
|---|---|---|---|---|---|---|---|
| 1 | 5.00 | 2.50 | 5.67 | 94.51 | 94.64 | 85.1 | 1.95 |
| 2 | 7.50 | 3.75 | 3.55 | 96.68 | 94.89 | 87.0 | 2.92 |

TABLE 1-continued

Propane-propylene system, Isothermal, D = 50% F, $P_H$ = 1 atm, $P_L$ = 0.01 atm

| Run | $F*10^4$ (mol/s) | $D*10^4$ (mol/s) | $R_E$ | $XC_3H_6$ (%) | $1-XC_3H_8$ (%) | $C_3H_6$ Recovery % | Productivity (mol/kg-h) |
|---|---|---|---|---|---|---|---|
| 3 | 9.4 | 4.70 | 2.63 | 97.83 | 95.04 | 88.1 | 3.65 |
| 4 | 11.25 | 5.63 | 2.04 | 98.59 | 95.22 | 88.7 | 4.38 |

TABLE 2

Methane-ethane system, Isothermal, D = 50% F, $P_H$ = 1 atm, $P_L$ = 0.01 atm

| Run | $F*10^4$ (mol/s) | $D*10^4$ (mol/s) | $R_E$ | $XN_2$ (%) | $1-XN_2$ (%) | Recovery | Productivity (mol/kg-h) |
|---|---|---|---|---|---|---|---|
| 1 | 0.78 | 0.62 | 9.20 | 99.92 | 99.00 | 99.9 | 0.15 |
| 2 | 1.56 | 1.23 | 4.10 | 99.92 | 98.80 | 99.9 | 0.30 |
| 3 | 0.312 | 2.46 | 1.47 | 97.80 | 97.00 | 97.8 | 0.59 |
| 4 | 4.68 | 3.70 | 0.52 | 92.60 | 74.00 | 92.6 | 0.89 |
| 5 | 6.25 | 4.94 | 0.10 | 89.31 | 68.00 | 89.3 | 1.19 |

TABLE 3

Oxygen-Nitrogen system, Isothermal, D = 79% F, $P_H$ = 1 atm, $P_L$ = 0.1 atm

| Run | $F*10^4$ (mol/s) | $D*10^4$ (mol/s) | $XCH_4$ (%) | $R_E$ | $R_R$ | $1-XCH_4$ (%) | $C_2H_6$ Recovery % | Productivity (mol/kg-h) |
|---|---|---|---|---|---|---|---|---|
| 1 | 6.25 | 3.12 | 91.6 | 2.960 | 0.158 | 98.18 | 88.0 | 2.57 |
| 2 | 12.50 | 6.25 | 93.9 | 1.000 | 0.083 | 98.17 | 93.0 | 5.13 |
| 3 | 18.75 | 9.38 | 95.3 | 0.361 | 0.056 | 98.15 | 95.3 | 7.69 |
| 4 | 21.88 | 10.94 | 95.6 | 0.174 | 0.048 | 98.13 | 95.0 | 8.97 |
| 5 | 25.00 | 12.50 | 95.1 | 0.025 | 0.041 | 98.12 | 95.1 | 10.26 |

The fractionation of the binary mixtures is achieved in the mass transfer zones of the stripping and enriching beds. The extract product (strongly adsorbed component) is recovered in the regeneration step and a part of it is sent as reflux to the enriching section. The raffinate product is recovered from the stripping bed and a part is used to purge the bed that underwent regeneration step.

Simulation of the scheme shown in FIG. 5 which emulates a SMB in two fixed beds with three moving ports each has been simulated and results given in Tables 4-6.

TABLE 4

Isothermal propylene (1)-propane (2) system with total waste stream recycled.
D = 50% F, $R_R$ = 0.1% B. $P_H$ = 5 atm, $P_L$ = 0.0001 atm

| F, LPM | D, mol/s $*10^3$ | $R_E$ | $Z_{,SS}$ mm | $Z_{,ES}$ mm | $XC_3H_6$ (%) | $XC_3H_8$ (%) | $C_3H_6$ Recovery (%) | Productivity mol/kg-h |
|---|---|---|---|---|---|---|---|---|
| 0.73 | 0.249 | 5.26 | 0.88 | 1.04 | 99.0 | 99.0 | 99.0 | 670.29 |
| 1.10 | 0.374 | 4.91 | 1.26 | 1.30 | 99.0 | 99.0 | 99.0 | 753.90 |
| 1.65 | 0.562 | 4.10 | 1.74 | 1.69 | 99.0 | 99.0 | 99.0 | 844.20 |
| 1.93 | 0.656 | 3.99 | 2.01 | 1.94 | 99.0 | 99.0 | 99.0 | 855.13 |
| 2.29 | 0.781 | 3.17 | 2.20 | 2.05 | 99.0 | 99.0 | 99.0 | 946.22 |

TABLE 5

Isothermal ethane (1)-methane (2) system with total waste stream recycled.
D = 50% F, $R_R$ = 0.1% B. $P_H$ = 1 atm, $P_L$ = 0.0001 atm

| F, LPM | D, mol/s $*10^3$ | $R_E$ | $Z_{,SS}$ mm | $Z_{,ES}$ mm | $XC_2H_6$ (%) | $XCH_4$ (%) | $C_2H_6$ Recovery (%) | Productivity mol/kg-h |
|---|---|---|---|---|---|---|---|---|
| 0.91 | 0.312 | 15.28 | 0.14 | 0.49 | 99.9 | 99.9 | 99.9 | 1613.36 |
| 1.83 | 0.624 | 7.10 | 0.16 | 0.47 | 99.9 | 99.9 | 99.9 | 3225.2 |
| 3.67 | 1.249 | 3.07 | 0.21 | 0.45 | 99.9 | 99.9 | 99.9 | 6159.7 |

TABLE 5-continued

Isothermal ethane (1)-methane (2) system with total waste stream recycled.
$D = 50\% F, R_R = 0.1\% B. P_H = 1 \text{ atm}, P_L = 0.0001 \text{ atm}$

| F, LPM | D, mol/s *$10^3$ | $R_E$ | $Z, _{SS}$ mm | $Z, _{ES}$ mm | $XC_2H_6$ (%) | $XCH_4$ (%) | $C_2H_6$ Recovery (%) | Productivity mol/kg-h |
|---|---|---|---|---|---|---|---|---|
| 6.00 | 2.044 | 1.51 | 0.29 | 0.42 | 99.9 | 99.9 | 99.9 | 9364.0 |
| 9.00 | 3.065 | 0.70 | 0.43 | 0.37 | 99.9 | 99.9 | 99.9 | 12461.0 |

TABLE 6

Isothermal nitrogen (1)-oxygen (2) system with total waste stream recycled.
$D = 79\% F, R_R = 0.1\% B. P_H = 5 \text{ atm}, P_L = 0.0001 \text{ atm}$

| F, LPM | D, mol/s *$10^3$ | $R_E$ | $Z, _{SS}$ mm | $Z, _{ES}$ mm | $XN_2$ (%) | $XO_2$ (%) | $N_2$ Recovery (%) | Productivity mol/kg-h |
|---|---|---|---|---|---|---|---|---|
| 0.229 | 0.123 | 5.8 | 0.11 | 0.15 | 99.0 | 99.0 | 99.0 | 1525 |
| 0.458 | 0.246 | 5.1 | 0.21 | 0.15 | 99.0 | 99.0 | 99.0 | 2193 |
| 0.687 | 0.370 | 4.1 | 0.28 | 0.20 | 99.0 | 99.0 | 99.0 | 2466 |
| 0.917 | 0.494 | 3.5 | 0.34 | 0.24 | 99.0 | 99.0 | 99.0 | 2722 |

4. Single Bed Chromatographic Separator for Separation of Liquid Mixtures with Four Moving-Port Systems Using an Elutant The process is, in fact, SORBEX. It is carried out using moving systems rather than with rotary valves, and an elutant as shown in FIG. 14. The single column (60) is divided into 4 different sections which are as follows:

I—Adsorption of B

II—Adsorption of A

III—Desorption of B

IV—Desorption of A

A pump (61) is used to transfer the elutant from one end to the other. This type of SORBEX system uses 4 moving ports.

5. Single\Multiple Bed Reactor Cum Separator

The gaseous reaction and separation can be carried out in series of beds with mixed catalyst and adsorbent particles. It is possible to drive the reaction to completion and separate the reactants and products. This eliminates, or considerably simplifies the down stream processes. This is likely to alter the way chemical processes are carried out. For instance, it is possible to feed $N_2$ and $H_2$ and obtain pure $NH_3$ from the reactor separator. The reactor cum separator with two beds having two moving ports each is shown in FIG. 15. The scheme for product regeneration by using elutant has been shown in the figure. However the regeneration can also be effected by pressure swing. The packed bed here acts as a reaction zone (71) as well as a stripping zone (72). When the mixture of the products is fed from the feed tank (73), the packed bed acts as reaction zone and when the elutant is fed from the elutant tank (74), the packed bed acts as stripping zone. The contents of the packed bed column is removed and collected in a product tank (75) from where it is sent for elutant separation.

6. Single Bed Beat Regenerator with Four Moving-Bed Systems

The exchange of heat between gas streams requires bulk equipment, as the heat transfer coefficient is very low. The exchange can be accomplished in two beds of solids with two-ports each as shown in FIG. 16. The packed bed column having multiple inlet means is operated as cooling zone (81) and as a heating zone (82). The hot gas is fed to the cooling zone and exhausted hot gas is removed from the cooling zone, while cold gas is fed into the heating zone and heat enriched gas is withdrawn.

We have simulated such a regenerator, which can replace the blast furnace stoves. There was 70 times volume reduction based on single bed heat regenerator modeled using Intraparticle Conduction model and 97 times volume reduction on a using Schumann model with axial dispersion.

Accordingly the present invention provides a novel process for gas fractionation emulating the hypersorber in fixed beds that can fractionate any gas mixtures; the said beds are filled with specific adsorbents for individual mixtures and range from activated carbon, silica gel, various variants of zeolite, cation impregnated n-complexed Alumina\silica based adsorbents.

A novel concept of moving port systems to bring out effective solid gas contact; the said moving port systems accomplish the realization of countercurrent solid-gas contact in moving beds with fixed beds only.

A method of injection and withdrawal with a pair of two tubes with different diameter having helical slot and straight slot wherein the rotation of either of the tubes will result in movement of the port from one end of the tube to the other and has an abrupt return to the starting position for the next movement; the gas\liquid to be distributed within the fixed bed is connected to the inside tube with helical slot and gas is distributed into the fixed bed through the port formed with the outside tube having straight slot.

A method of injection and withdrawal with a pair of two tubes with different diameter; the bigger diameter tube being the outer tube with perforations and the inner tube connected to the fluid that is to be distributed has a piston like appearance; gas/liquids flows out only through the perforations in the outer tube that overlap with the opening in the inner tube.

A novel process of fractionating any gas mixture in four fixed beds with or without moving ports wherein in a step of a cycle Bed 1 undergoes the High Pressure Adsorption\Stripping Step, Bed 2 undergoes the High Pressure Extract Reflux\Enriching Step, Bed 3 undergoes the Low Pressure Regeneration Step, and Bed 4 undergoes both the Low pressure Raffinate Purge with Total Recycle and the High Pressure Raffinate Reflux Step; after the said processes are completed in each bed the flow streams in and out of each bed are redirected such that in the next step of the cycle the processes that occurred in Bed 1, Bed 2, Bed 3 and Bed 4 of the previous step are switched and carried out in Bed 2, Bed 3, Bed 4 and Bed 1 correspondingly; after two more such shifts each bed would have performed all the individual steps and a cycle is complete; and the time to complete this is the cycle time. In a step of a cycle—

(a) Bed 1 with or without moving ports prior to be fed with the feed is presaturated with the raffinate product in a direction co-current to the direction of feed in the High pressure raffinate reflux step; with accomplishment of the said Presaturation the feed is fed with moving ports held in a fixed position in the bed or moving across the bed; the said feeding continued until breakthrough of the mass transfer zone is impending; the effluent from this step collected as raffinate product and a part of it is used for the low pressure and high pressure raffinate reflux.

(b) Bed 2 with or without moving ports is refluxed with the Extract product in a direction co-current to the direction of feed; prior to this reflux step the bed has been saturated with feed during High Pressure adsorption\Stripping Step of the previous step of the cycle; the said reflux saturates the bed with extract product; the said reflux shall be made with moving ports held in a fixed position in the bed or moving across the bed; the effluent of this reflux step is relatively rich in the extract component than with the actual feed; the said effluent is totally recycled back along with the feed for the High Pressure adsorption\Stripping Step; the said reflux step is continued until the mass transfer zone generated in the bed breakthrough across the bed.

(c) Bed 3 with or without moving ports with the entire inlet to it ceased is regenerated by reducing the pressure to subatmospheric and the effluent is drawn as the extract product in a direction co-current to the direction of feed; the said bed is saturated with the extract component during the High Pressure Extract Reflux\Enriching Step of the previous step of the cycle; the said regeneration is done by withholding the moving ports at a fixed position; the said effluent drawn as the extract product is compressed and part of it used as reflux for the High Pressure Extract Reflux\Enriching Step.

(d) Bed 4 with or without moving ports is refluxed with the raffinate product at low pressure; the effluent of the said low pressure reflux is compressed and totally recycled back along with the feed for the High Pressure adsorption\Stripping Step; the said low pressure reflux displaces off the extract component that remain unregenerated in bed during the Low Pressure Regeneration Step of the previous step of the cycle; after the said Low pressure Raffinate Purge with Total Recycle and with the entire streams out of the be ceased the said bed is refluxed further with the raffinate to pressurize the bed to make it ready for the next High Pressure adsorption\Stripping Step; the said refluxes of the raffinate both at low as well as high pressure is accomplished by withholding the moving ports at a fixed position.

Variant of the fractionation process of gas mixtures in fixed bed with more than one moving ports; one of the said variant shall be accomplished in two fixed beds with two moving ports each with one of the said beds undergoing separation has active moving ports and the other bed undergoing regeneration has inactive moving ports; the other variant same as the previous one but for the three moving ports in each bed.

Application of the moving port for Sorbex like separation in fixed beds without rotary valves; the said application is accomplished with four moving ports in a fixed bed which partitions the bed into four distinct zone and thereby perform the Sorbex like process without rotary valves.

Application of the moving port to carry out a chemical reaction and separation concurrently in Single\Multiple bed Reactor cum Separator; the said reaction is accomplished in a reaction zone formed between two moving ports with the reactants being fed with one moving port and the unreacted reactants removed through another; the said separation is accomplished in a separating zone formed by another two moving ports where the product that is adsorbed in the bed is regenerated either by pressure swing or by using an elutant; the said process with regeneration of product from the fixed bed by pressure swing can be accomplished only in multiple beds and the least with two beds. Application of the moving port to carry out heat exchange in a two bed regenerative type heat exchanger; the said heat exchange is accomplished with four moving ports which form two distinct zones with a pair each; the hot gas to be cooled is fed to the cooling zone through a moving port where the bed is heated and the effluent cold gas is removed out of the zone through another moving port which along with the first moving port has formed the cooling zone; the cold gas to be heated is fed through the moving port which along with another moving port that carries the effluent hot gas forms the heating zone; the said heating and cooling zones are not allowed to mix with each other having a strategic control over the pressure in the said zones.

The invention claimed is:

1. A fixed bed hypersorber effectuating clean separation of a gas mixture by countercurrent solid-gas/solid-liquid contacting, said hypersorber comprising:
   a) one or more columns comprising solid absorbent/adsorbent material in the form of packed bed section, and
   b) one or more piston-like moving port fluid injection and withdrawal systems incorporated inside the column for injecting and withdrawing the gas/liquid to be purified; the said piston like moving port comprises a perforated outer tube encircling a piston head perforated along the circumference; said piston head being attached to cylindrical annulus head for preventing back entry of the injected fluids and a cylindrical annulus head enclosure being provided outside the bed to guide the movement of the cylindrical annulus head.

2. A fixed bed hypersorber as claimed in claim 1, wherein the holes are provided on a circumferential side of the piston head.

3. A fixed bed hypersorber as claimed in claim 1, wherein the hollow piston is connected to a supply of the mixture of fluids.

4. A fixed bed hypersorber as claimed in claim 1, wherein the fluids are fed to the piston at elevated pressure.

5. A fixed bed hypersorber as claimed in claim 1, wherein the piston is attached to a motor through a connecting means for providing to and fro motion to the piston.

6. A fixed bed hypersorber as claimed in claim 5, wherein the piston is attached to a motor through a linear screw for providing to and fro motion to the piston.

7. A process for fractionation of a mixture of fluids, said process comprising the steps of:
   (a) providing one or more hypersorbers, each of the said hypersorbers comprising one or more variable inlet means for influx of the mixture of fluids, one or more fixed beds filled with one or more adsorbers being placed in proximity of the inlet means, and at least two outlet means through which the fractionated fluids can be withdrawn, wherein the variable inlet means comprises of one or more piston-like moving port fluid injection and withdrawal systems; the said piston like moving port comprises of a perforated outer tube encircling a piston head perforated along the circumference; said piston head being attached to a cylindrical annulus head for preventing back entry of the injected fluids and a cylindrical annulus head enclosure being provided outside the bed to guide the movement of the cylindrical annulus head;

(b) introducing the mixture of fluids to be fractionated into the variable inlet means in order to form an axial and radial flow of the fluids, wherein the axial and radial flow of the mixture of fluids is such that the fluids come out of the inlet means from different controllable locations;

(c) contacting the mixture of fluids to be fractionated coming out of the variable inlet means with the fixed bed filled with the adsorbers saturated with the raffinate component to adsorb an extract component preferentially from the mixture of the fluids and to provide a substantially pure raffinate component;

(d) removing the substantially pure raffinate component of step (c) from at least one of the said outlet means;

(e) extracting product reflux from at least one of said inlet means in the portion of the bed saturated with the feed mixture such that the said reflux saturates the bed with the extract component;

(f) desorbing the extract component from the fixed adsorbent bed saturated with the extract to obtain a substantially pure extract component; and (g) regenerating the desorbed fixed adsorbent bed by purge and pressurizing purging the same with raffinate component.

8. A process as claimed in claim 7, wherein the mixture of fluids to be fractionated is selected from the group consisting of a mixture of two or more gases, a mixture of one or more gases and one or more liquids, and a mixture of two or more liquids.

9. A process as claimed in claim 7, wherein the holes are provided on a circumferential side adjuvant to the cylindrical annular head.

10. A process as claimed in claim 7, wherein the hollow piston is connected to a supply of the mixture of fluids.

11. A process as claimed in claim 7, wherein the mixture of fluids are fed to the piston at elevated pressure.

12. A process as claimed in claim 7, wherein the piston is attached to a motor through a connecting means for providing back and forth motion to the piston.

13. A process as claimed in claim 12, wherein the piston is attached to a motor through a linear screw for providing back and forth motion to the piston.

14. A process for fractionation of a mixture of fluids using 4 identical fixed bed hypersorbers, BED 1, BED 2, BED 3 and BED 4, each hypersorber having a moving port as claimed in claim 1, said process comprising the steps of:

(a) carrying out a step of high pressure adsorption in BED 1, the step of high pressure extract reflux in BED 2, the step of low pressure regeneration in BED 3 and the step of low pressure raffinate purge with total recycle and high pressure raffinate reflux in BED 4 simultaneously;

(b) carrying out a step of high pressure adsorption in BED 4, the step of high pressure extract reflux in BED 1, the step of low pressure regeneration in BED 2 and the step of low pressure raffinate purge with total recycle and high pressure raffinate reflux in BED 3 simultaneously;

(c) carrying out a step of high pressure adsorption in BED 3, the step of high pressure extract reflux in BED 4, the step of low pressure regeneration in BED 1 and the step of low pressure raffinate purge with total recycle and high pressure raffinate reflux in BED 2 simultaneously, and (d) carrying out a step of high pressure adsorption in BED 2, the step of high pressure extract reflux in BED 3, the step of low pressure regeneration in BED 4 and the step of low pressure raffinate purge with total recycle and high pressure raffinate reflux in BED 1 simultaneously.

15. A process as claimed in claim 14, wherein the moving port piston provided in the fixed hypersorber is optionally held stationary at one location.

16. A process for fractionation of a mixture of fluids using 2 identical fixed bed hypersorbers, BED 1 and BED 2, each hypersorber having two or three moving ports as claimed in claim 1, said process comprising the steps of:

(a) carrying out a step of separation in BED 1 and the step of regeneration in BED 2 simultaneously, wherein the step of separation is carried out in BED 1 by dividing BED 1 into a high pressure adsorption zone and a high pressure extract reflux zone and the step of regeneration is carried out in BED 2 by dividing BED 2 into a low pressure regeneration zone and a low pressure raffinate purge with total recycle and high pressure raffinate reflux zone, simultaneously; and (b) switching the process being carried out in the BEDs such that the separation step is carried out in BED 2 and the step of regeneration is carried out in BED 1.

17. A process as claimed in claim 16, wherein the step of separation is carried out by activating the ports and the step of regeneration is carried out with the ports being held inactive.

18. A process for fractionation of a mixture of fluids, said process comprising the steps of:

(a) providing one or more hypersorbers, each of the hypersorbers comprising one or more variable inlet means for influx of the mixture of fluids, one or more fixed beds filled with one or more adsorbers being placed in proximity of the inlet means, and at least two outlets means through which the fractionated fluids can be withdrawn, wherein the variable inlet means comprises one or more piston-like moving port fluid injection and withdrawal systems, the said piston-like moving port comprises of a pair of tubes arranged in a concentric fashion, and being provided with one or more slots;

(b) introducing the mixture of fluids to be fractionated into the variable inlet means in order to form an axial and radial flow of the fluids, wherein the axial and radial flow of the mixture of fluids is such that the fluids come out of the inlet means from different controllable locations;

(c) contacting the mixture of fluids to be fractionated coming out of the variable inlet means with the fixed bed filled with the adsorbers saturated with the raffinate component to adsorb an extract component preferentially from the mixture of the fluids and to provide a substantially pure raffinate component;

(d) removing the substantially pure raffinate component of step (c) from at least one of the said outlet means;

(e) extracting product reflux from at least one of said inlet means in the portion of the bed saturated with the feed mixture such that the said reflux saturates the bed with the extract component;

(f) desorbing the extract component from the fixed adsorbent bed saturated with the extract to obtain a substantially pure extract component; and (g) regenerating the desorbed fixed adsorbent bed by purge and pressurizing purging the same with raffinate component.

19. A process as claimed in claim 18, wherein the variable inlet means for influx of the mixture of fluids comprises of a pair of concentric tubes wherein an inner tube is provided with a traverse slot running parallel to a vertical axis of the tube and an outer tube provided with a helical slot running parallel to a vertical axis of the tube or vice versa such that a trapezoidal opening is formed where both the slots overlap.

20. A process as claimed in claim 19, wherein outer tube is rotated with respect to the inner tube to move the trapezoidal opening from one end of the tube to the other.

21. A process for fractionation of a mixture of fluids, said process comprising the steps of:
   (a) providing one or more hypersorbers, each of the hypersorbers comprising one or more variable inlet means for influx of the mixture of fluids, one or more fixed beds filled with one or more adsorbers being placed in proximity of the inlet means, and at least two outlet means through which the fractionated fluids can be withdrawn, wherein the variable inlet means comprises of a pair of tubes arranged in a concentric fashion such that an inner tube is provided with a series of valves on its outer surface and an outer tube is provided with a means for opening the valves in a predetermined fashion on its interior surface;
   (b) introducing the mixture of fluids to be fractionated into the variable inlet means in order to form an axial and radial flow of the fluids, wherein the axial and radial flow of the mixture of fluids is such that the fluids come out of the inlet means from different controllable locations;
   (c) contacting the mixture of fluids to be fractionated coming out of the variable inlet means with the fixed bed filled with the adsorbers saturated with the raffinate component to adsorb an extract component preferentially from the mixture of the fluids and to provide a substantially pure raffinate component;
   (d) removing the substantially pure raffinate component of step (c) from at least one of the said outlet means;
   (e) extracting product reflux from at least one of said inlet means in the portion of the bed saturated with the feed mixture such that the said reflux saturates the bed with the extract component;
   (f) desorbing the extract component from the fixed adsorbent bed saturated with the extract to obtain substantially pure extract component; and
   (g) regenerating the desorbed fixed adsorbent bed by purge and pressurizing purging the same with raffinate component.

22. A process as claimed in claim 21, wherein variable inlet means for influx of the mixture of fluids comprises of a pair of tubes arranged in a concentric fashion such that an inner tube is provided with a series of valves on its outer surface and an outer tube is provided with a means for opening the valves in a predetermined fashion on its interior surface.

23. A process as claimed in claim 22, wherein the variable inlet means for influx of the mixture of fluids comprises of a pair of tubes arranged in a concentric fashion such that an inner tube is provided with a series of valves on its outer surface and an outer tube is provided with a helical strip on its interior surface for opening the valves in a sequential fashion.

* * * * *